(12) United States Patent
Kang et al.

(10) Patent No.: US 7,760,854 B2
(45) Date of Patent: Jul. 20, 2010

(54) METHOD AND DEVICE OF IRRADIATION OF LOGS WITH X-RAY AS A PHYTOSANITARY TREATMENT

(75) Inventors: Kejun Kang, Beijing (CN); Haifeng Hu, Beijing (CN); Chuanxiang Tang, Beijing (CN); Yuanjing Li, Beijing (CN); Qitian Miao, Beijing (CN); Huayi Zhang, Beijing (CN); Junli Li, Beijing (CN); Zhiqiang Chen, Beijing (CN); Ming Hu, Beijing (CN); Ming Huang, Beijing (CN); Yaohong Liu, Beijing (CN); Wanlong Wu, Beijing (CN); Hui Zhang, Beijing (CN); Shenjin Ming, Beijing (CN)

(73) Assignees: Tsinghua University, Beijing (CN); Nuctech Comany Limited, Beijing (CN)

( * ) Notice: Subject to any disclaimer, the term of this patent is extended or adjusted under 35 U.S.C. 154(b) by 181 days.

(21) Appl. No.: 12/101,726

(22) Filed: Apr. 11, 2008

(65) Prior Publication Data

US 2008/0253517 A1    Oct. 16, 2008

(30) Foreign Application Priority Data

Apr. 12, 2007    (CN)    ......................... 2007 1 0065383

(51) Int. Cl.
*G21K 5/00* (2006.01)
*G01N 23/04* (2006.01)

(52) U.S. Cl. .......................................... 378/64; 378/57
(58) Field of Classification Search ................... 378/57, 378/58, 62, 64, 68, 69
See application file for complete search history.

(56) References Cited

U.S. PATENT DOCUMENTS

2007/0165777 A1*    7/2007    Anwar et al. ................... 378/57

* cited by examiner

*Primary Examiner*—Irakli Kiknadze
(74) *Attorney, Agent, or Firm*—Kenyon & Kenyon LLP

(57) ABSTRACT

A method for conducting irradiation of all logs of a whole vehicle with X-rays as a phytosanitary treatment may include: connecting a traction device and a goods carrying vehicle outside a shielding door; opening the door; the traction device pulling the vehicle into a tunnel; closing the shielding door; upon the vehicle reaching an irradiation region, accelerators generating X-rays; the traction device pulling the vehicle to pass through the irradiation region; stopping the X-rays; opening the door; the traction device pulling the vehicle away from the irradiation treatment tunnel; and disconnecting the traction device from the vehicle. A device may include a shielding structure, a tunnel formed therethrough; a rail along the tunnel; accelerators within the tunnel; and a traction device for pulling a vehicle carrying goods for quarantine treatment, the accelerators symmetrically arranged at both sides of and on the top of an irradiation region in the tunnel.

23 Claims, 4 Drawing Sheets

METHOD AND DEVICE OF IRRADIATION OF LOGS WITH X-RAY AS A PHYTOSANITARY TREATMENT

FIELD OF THE INVENTION

The present invention relates to a technical field of quarantine treatment of a farming and forestry product for pest control, and more particularly, to a method and a device of irradiation of logs with X-ray as a phytosanitary treatment.

BACKGROUND INFORMATION

With rapid development of the farming and forestry, it is seriously desired to strengthen the inspection and quarantine of the imported logs and wood products to prevent spread of risky pests. Conventional quarantine treatment of the logs employs a method of fumigation by Methyl Bromide. This method has distinct shortcomings and limitations. Methyl Bromide would deplete the ozone layer of the atmosphere, and, according to the amendment to "The Montreal Protocol on Substances that Deplete the Ozone Layer" at Copenhagen (1992), in order to protect the ozone layer of the atmosphere, each developed country of the parties of the Protocol shall ensure that for the twelve-month period commencing on Jan. 1, 2005 and in each twelve-month period thereafter, its calculated level of consumption of Methyl Bromide does not exceed zero, and, each developing country shall ensure that for the twelve-month period commencing on Jan. 1, 2015 and in each twelve-month period thereafter, its calculated level of consumption of Methyl Bromide does not exceed zero. Fumigation by Methyl Bromide is infeasible at a temperature below 5° C. Methyl Bromide is poisonous to nerve, and would be released to the atmosphere after the treatment of fumigation, contaminating the living environment of human beings. Phytosanitary treatment by fumigation with Methyl Bromide is fairly inefficient, because it needs over 16 hours to seal the logs to complete one treatment.

SUMMARY OF THE INVENTION

The present invention provides a method and a device which solves the above disadvantages. The method and device include irradiation of logs with X-ray as a phytosanitary treatment. The method and device employ a plurality of linear accelerators (LINACs) to generate X-ray for conducting irradiation treatment of logs, having the absorbed dose in the logs distributed as evenly as possible, and the minimum of the absorbed dose reach a certain level, resulting in sterility or death of the pests, achieving the purpose of phytosanitary treatment.

The present invention provides a method of irradiation with X-ray as a phytosanitary treatment. The method includes steps of: connecting a traction device and a goods carrying vehicle outside a shielding door; opening the shielding door; pulling the vehicle into an irradiation tunnel by the traction device; closing the shielding door; when the vehicle reaches the irradiation region, X-ray beams generated by accelerators, pulling the vehicle passing through the irradiation region by the traction device to complete the quarantine treatment of the whole vehicle by irradiation, at which point X-ray stops; opening the shielding door; pulling the vehicle away from the irradiation tunnel by the traction device; and disconnecting the traction device from the vehicle.

According to a preferred embodiment of the invention, in the step of pulling the vehicle passing through the irradiation region, the traction device pulls the vehicle passing through the radiation region reciprocatingly to receive irradiation twice, in order to ensure the minimum absorbed dose in the logs reach the phytosanitary requirement.

According to a preferred embodiment of the invention, the accelerators are a plurality of accelerators arranged symmetrically at both sides and the top of the irradiation region in the tunnel on the cross section perpendicular to the spread direction of the tunnel, in order to generate an X-ray radiation field in the logs as even as possible.

According to a preferred embodiment of the invention, the irradiation treatment is conducted for all the logs carried in the vehicle.

According to a preferred embodiment of the invention, the plurality of accelerators amounts to five, wherein two are set at the left side of the tunnel, two are set at right side of the tunnel, and one is set at the top of the tunnel.

According to a preferred embodiment of the invention, the accelerators are staggered along the spread direction of the tunnel.

According to a preferred embodiment of the invention, each accelerator is configured to generate X-ray by electron beams hitting metal target with different scanning angles, in order to generate an X-ray radiation field in the logs as evenly as possible.

The present invention provides a device for conducting irradiation as a phytosanitary treatment with X-ray, including a shielding structure, a tunnel formed in the shielding structure, a rail spread along the tunnel, accelerators surrounding the tunnel, and a traction device for pulling a vehicle carrying goods. The accelerators are a plurality of accelerators symmetrically arranged at both sides and on the top of the irradiation region in the tunnel on the cross section perpendicular to the spread direction of the tunnel.

According to a preferred embodiment of the invention, the plurality of accelerators amounts to five, wherein two are set at the left side of the tunnel, two are set at right side of the tunnel, and one is set at the top of the tunnel.

According to a preferred embodiment of the invention, the goods for quarantine treatment include all logs of the whole vehicle.

According to a preferred embodiment of the invention, the shielding structure includes: a shielding door at one end of the tunnel; shielding walls forming the tunnel; a maze for providing entrance to the tunnel; a radiation source shielding chamber located in the middle of the tunnel for lowering the leakage radiation of the X-ray generated by the accelerators; and a device chamber door for providing entrance to the radiation source shielding chamber for devices and maintenance staff; wherein the shielding walls are located at both sides of and at one end of the tunnel, and the shielding door is located at the other end of the tunnel.

According to a preferred embodiment of the invention, the shielding door, device chamber door, and maze are provided with safety interlock devices respectively for avoiding incident caused by unintentional entry of people.

According to a preferred embodiment of the invention, the shielding door, shielding walls, maze and radiation source shielding chamber form a closed region, which is designated as the radiation controlled area.

According to a preferred embodiment of the invention, a number of buttresses are provided on the shielding walls along the spread direction of the tunnel to lower the radiation level outside the shielding door caused by the scattering on the shielding walls.

According to a preferred embodiment of the invention, the traction device includes a traction locomotive, a hook, a current collector, and a sliding guide rail; wherein, the sliding guide rail is fixed to the ground along the spread direction of the tunnel; the traction device can realize automatic connection with the vehicle via the hook; and the current collector is installed on a side of the traction locomotive for contact with the sliding guide rail for keeping communication and supplying the driving power.

According to a preferred embodiment of the invention, the traction device further includes an anti-collision device fixed to one end of the rail in the tunnel for preventing collision between the traction device and the closed end of the tunnel.

According to a preferred embodiment of the invention, the traction locomotive is an unmanned automatic driving locomotive.

According to a preferred embodiment of the invention, each accelerator is configured to generate X-ray by electron beams hitting a metal target with different scanning angles, in order to generate an X-ray radiation field in the logs as evenly as possible.

According to a preferred embodiment of the invention, energy of the accelerators is selected from 10 MeV to 16 MeV.

Embodiments of the present invention use the strong penetrating capacity of the X-ray to exert biologic effects on the pests directly or indirectly, achieving the quarantine purpose by rendering the pests in the logs sterile or unable to develop to an adult, or even killing the pests. Compared to the conventional technique, an irradiation treatment of the present invention is more effective, reliable, fast, safe, pollution free, and easy to operate. Additionally, the vehicle carrying the logs can pass through the radiation region reciprocatingly and to receive irradiation twice, which both shortens the length of the tunnel, decreasing the cost accordingly, and increases the speed of the vehicle, making the design simplified. Furthermore, one end of the tunnel can be closed, therefore decreasing the cost for radiation protection, and facilitating the dispatching work of the locomotive.

Additionally, the accelerator used by the present invention is an electrical device which will not pollute the atmosphere and the environment. Furthermore, application of the invention is not influenced by the environmental temperature, and, as long as the power supply meets the requirement, application of the invention is feasible. The accelerator only generates the X-ray during operation, and will not generate X-ray after being powered off. Therefore, there exists no problem of waste treatment, which would otherwise result in the case of using the radioisotope source.

DETAILED DESCRIPTION

The present invention will be described according to exemplary embodiments thereof. However, the invention is not limited thereto. The invention is illustrated as a vehicle for carrying the logs, but can be applied to other vehicles which are capable of carrying other goods as well.

Figure 1:
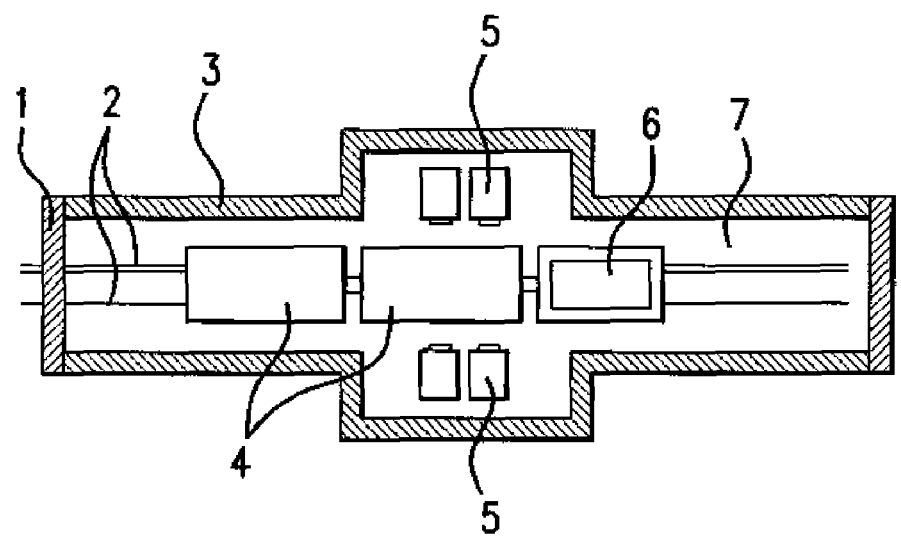
FIG. 1 is a principle view of the whole configuration of the device according to an example embodiment of the present invention.

FIG. 1 shows the whole structural principle of the device of the invention. The device for carrying out the irradiation treatment of the logs with X-ray mainly includes a rail 2, a shielding structure 3, accelerators 5, a traction device 6, and a tunnel 7. The tunnel 7 is formed in the shielding structure 3. The rail 2 is provided in the tunnel 7 and can extend to the outside of the tunnel 7. The accelerators 5 are set at both sides of and on the top of the tunnel 7 in the middle of the tunnel 7. According to the capacity of quarantine requirement, the accelerators 5 can be provided as several units, each unit can includes several accelerators. The shielding structure 3 has the X-ray and neutron protection ability for shielding the leakage and scattering radiation of the X-ray generated by the accelerators and other secondary rays to ensure safety of the operator and public, and safety of the device. The traction device 6 can pull the log carrying vehicle 4 to move along the rail 2.

The penetration capacity of the high energy X-ray is extremely strong which is well applicable for irradiation treatment to all the logs carried in a vehicle. However, the X-ray suffers exponential attenuation in objects, while the distribution of the X-ray generated by electrons hitting the metal target in the LINAC is extremely uneven in each spatial direction. Therefore, the number and arrangement of the accelerators should be properly optimized to efficiently use the energy while improving the economic performance. The inventor conducted a numerous calculations and experiments, and further in view of the operability, determined that it is advantageous to employ 5 accelerators as one unit in a preferred embodiment which is arranged in the positions as stated below to obtain a good processing result. It should be understood that the provision of 5 accelerators is just an example, and other numbers and arrangements of the accelerators also fall into the scope of the present invention.

Figure 2:
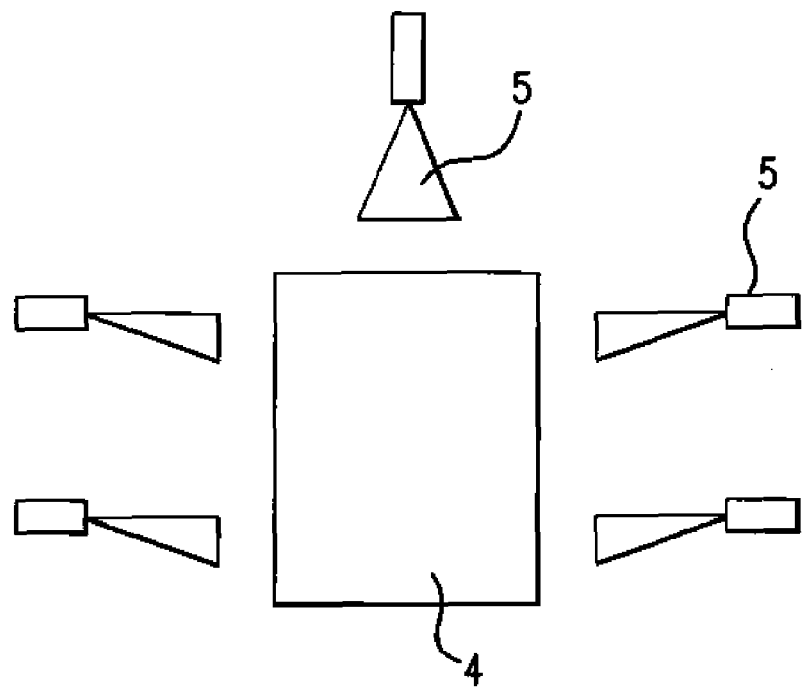
FIG. 2 is an illustration of a layout of accelerators according to an example embodiment of the present invention.

As shown in FIG. 2, the accelerators 5 of the invention are installed in the middle of the tunnel 7 which forms an X-ray radiation field, designated as an irradiation region, during operation. In the preferred embodiment, five accelerators are employed as one unit and are arranged at both sides of and on the top of the tunnel 7 respectively. With respect to a cross sectional plane perpendicular to the advancing direction of the log, as shown in FIG. 2, the five accelerators are arranged symmetrically between the left and right such that two are positioned at the left, two are positioned at the right, and one is positioned at the top. In the advancing direction of the log, the target positions of the accelerators are staggered on both sides of the irradiation region (as shown in FIG. 1). Each accelerator is configured to generate X-ray by electron beams hitting a metal target with different scanning angles, in order to make the distribution of the absorbed dose in the logs as even as possible. The number of units of the accelerators can be increased properly according to requirement of the processing capacity.

Figure 3:
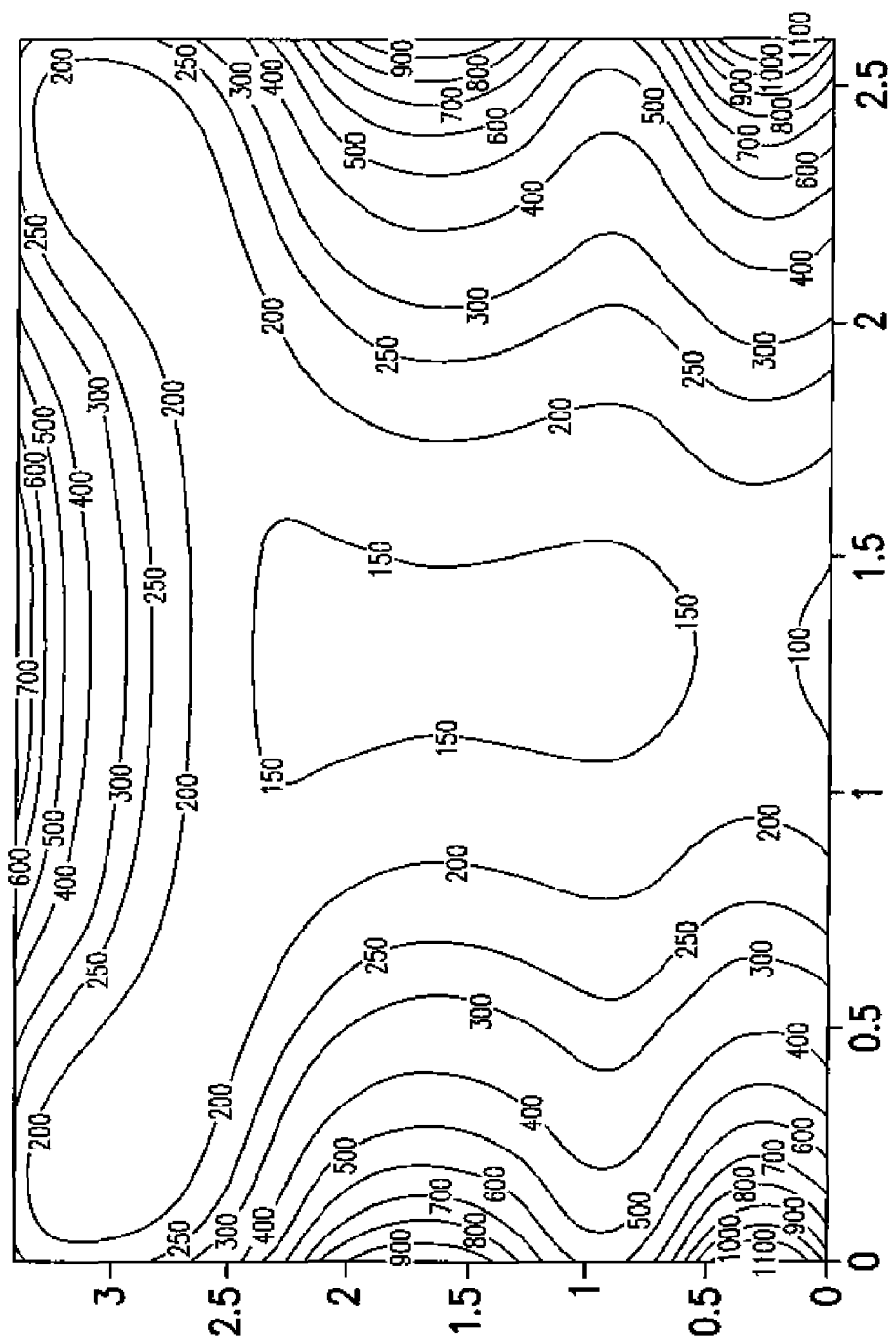
FIG. 3 is an illustration of a contour map of the distribution of an absorbed dose in a vehicle after irradiation by five accelerators according to an example embodiment of the present invention.

FIG. 3 is an illustration of a contour map of the distribution of the absorbed dose in a vehicle after irradiation by five accelerators arranged according to the manner described above. It can be seen that, after irradiation of the five accelerators arranged as shown in FIG. 3, the distribution of absorbed dose is generally even, and a better effect of irradiation treatment can be attained.

It should be noted that the accelerator used by the present invention is an electrical device, the application of which is not influenced by the environmental temperature, and, as long as the power supply meets the requirement, application of the invention is feasible. The accelerator only generates the X-ray during operation, and will not generate X-ray after being turned off. Therefore, there exists no problem of waste treatment, which would otherwise result in the case of using the radioisotope source.

However, it should be noted that, a photonuclear reaction will take place when the high energy X-ray meets the element in the irradiated mass, generating a radioisotope as a result. Furthermore, the X-ray may react with mass, resulting in neutron activation. All these reactions can form induced radioactivity, and the higher the energy is, the more the induced radioactivity will be. Meanwhile, selection of the accelerator with too low energy will decrease the processing efficiency of the system. Taking into account society safety, people safety, and device safety, while at the same time considering the processing efficiency, the inventor evaluated accurately the influences of the induced radioactivity of X-ray with different energies and found that it is preferable to select the accelerator with energy ranging from 10 to 16 MeV. Therefore, a preferred embodiment of the present invention is to select the accelerator with energy ranging from 10 to 16 MeV, to ensure the induced radioactivity generated will not harm the operator and the public.

Figure 4:
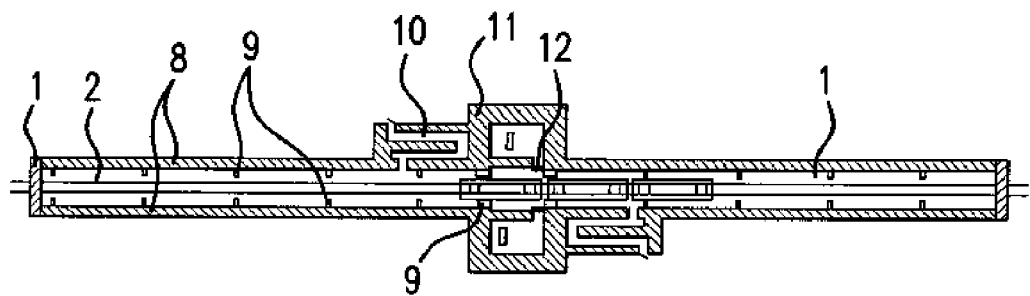
FIG. 4 is an illustration of a shielding structure according to an example embodiment of the present invention.

Referring to FIG. 4, which shows the exemplified shielding structure 3 of the present invention, the shielding structure 3 includes shielding door 1, shielding walls 8, maze 10, radiation source shielding chamber 11, and device chamber door 12. The shielding door 1 is provided at the entrance of the tunnel 7; the rail 2 extends from the shielding door 1 into the tunnel 7, and can extend further to the outside of the tunnel 7. The radiation source shielding chamber 11 can be located in the middle of the tunnel 7, and the radiation source can be positioned in the middle of the tunnel 7 during operation. The device chamber door 12 provides entrance to the radiation source shielding chamber 11 for the device and the maintenance staff. The device chamber door 12 is provided with a safety interlock device to avoid unintentional entry. The shielding walls 8 can be provided at both sides of the tunnel 7, and can be provided at the end of the tunnel 7 which is opposite to the position where the shielding door 1 is located. The shielding walls 8 are also provided at the top of the tunnel 7.

For safety, the shielding door 1 is in a normally closed state, and will be automatically opened only when the log carrying vehicle is passing by. The door is provided with a safety interlock device to avoid incident caused by unintentional access of people.

Figure 5:
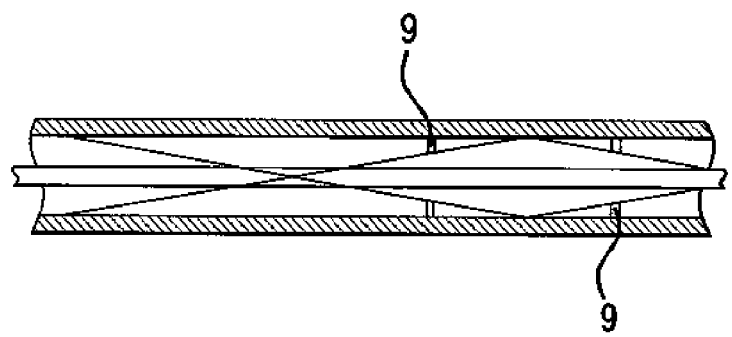
FIG. 5 is an illustration showing the function of buttresses on the shielding walls according to an example embodiment of the present invention.

The shielding walls 8 can be provided with a certain number of buttresses or barriers 9 along the spread direction of the tunnel to lower the radiation level outside the shielding door caused by the scattering on the shielding walls. The function of the buttresses on the shielding walls 8 is shown in FIG. 5. Because of the existence of the buttresses 9, most of the X-ray from the radiation source cannot reach the shielding door 1 after being scattered on the shielding walls 8.

The maze 10 provides entrance for the people entering the tunnel 7. The maze 10 is provided with a safety interlock device to avoid unintentional access of people. The shielding door 1, shielding walls 8, maze 10, and radiation source shielding chamber 11 constitute a closed region, which is designated as the radiation controlled area.

The present invention relates to direct irradiation to the logs of the whole vehicle, which requires an irradiation tunnel with large cross section for access of the locomotive. Therefore, the conventional maze structure cannot be used as a part of the tunnel. Consequently, the present invention employs the shielding structure containing the tunnel walls with buttresses (barriers) and the shielding door to meet the safety requirement at the entrance and exit, as well as other portions outside the tunnel. Therefore, when the accelerators are in operation, the leakage radiation level outside the tunnel meets the relevant requirements according to the international regulations ("International Basic Safety Standards for Protection Against Ionizing Radiation and for the Safety of Radiation Sources," IAEA, No. 115, 1996), thus ensuring safety of public and operators.

Figure 6:
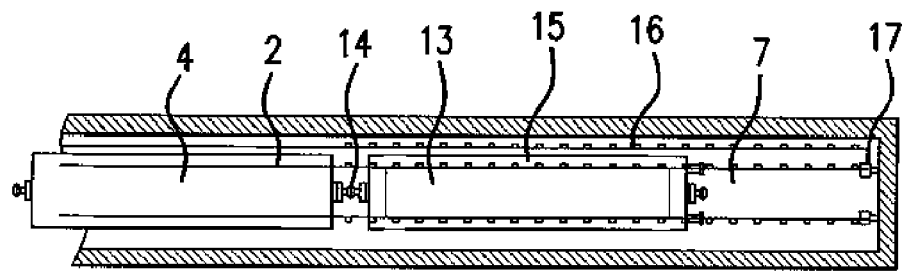
FIG. 6 is an illustration showing the structural principle of the traction device according to an example embodiment of the present invention.

The structural principle of the traction device of the invention is shown in FIG. 6. The exemplified traction device 6 includes a traction locomotive 13, a hook 14, a current collector 15, a sliding guide rail 16, and an anti-collision device 17. The sliding guide rail 16 is fixed to the ground along the spread direction of the tunnel 7 for providing electrical and communication connection with the current collector 15 of the traction locomotive 13. The current collector 15 is provided at one side of the traction locomotive 13 to be in contact with the sliding guide rail 16 to keep the communication and supply of the driving power. The anti-collision device 17 is fixed to the end of the rail in the tunnel, serving as the mechanical protection of the present system, and can be considered as a part of the traction device. The traction locomotive 13 can realize automatic or manual hooking with the log carrying vehicle 4 via the hook 14.

In the present embodiment, the traction locomotive is an unmanned automatic driving locomotive. In operation, the traction locomotive can either pull the log carrying vehicle at a relatively low constant speed through the irradiation region to expose the logs as evenly as possible, or pull/push the log carrying vehicle in/out the tunnel at a relatively high speed to increase the operating efficiency. In the preferred embodiment of the present invention, the traction locomotive can pull the log carrying vehicle passing through the radiation region reciprocatingly to receive irradiation twice to ensure the minimum absorbed dose in the logs reaches the phytosanitary requirement, realizing the purpose of simplifying the design and reducing the cost consequently.

Alternatively, according to another embodiment of the present invention, the tunnel 7 can be provided with shielding doors 1 at both ends thereof. Therefore, the traction locomotive can pull the log carrying vehicle passing through the radiation region once (or several times reciprocatingly) from the shielding door at the entrance of the tunnel 7 to the shielding door at the exit of the tunnel 7. In the present embodiment, the provision of the anti-collision device 17 can vary from the previously described embodiment. For example, the anti-collision device 17 can be omitted in an example embodiment.

Figure 7:
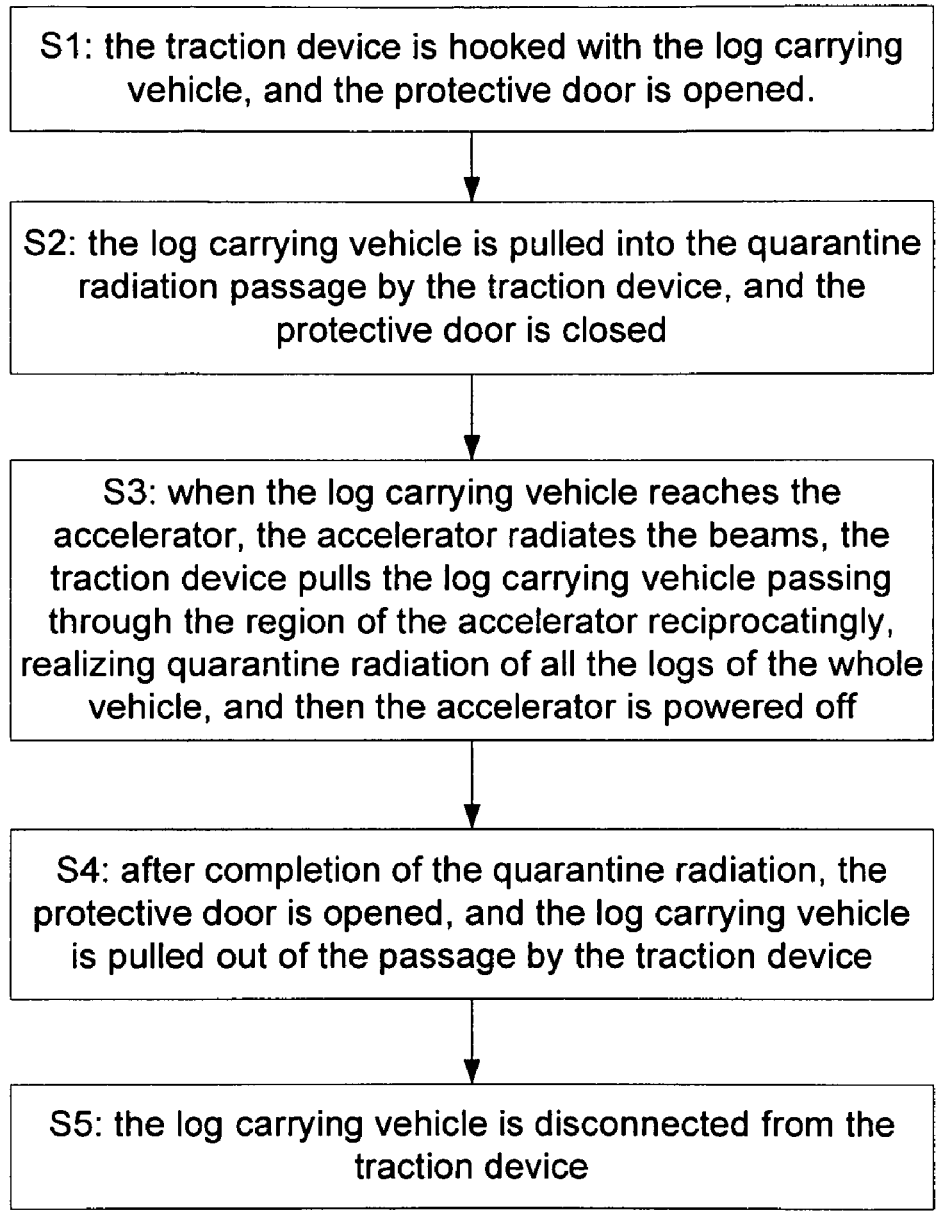
FIG. 7 is a flowchart showing an exemplary method according to the present invention.

FIG. 7 shows a flowchart of the preferred embodiment of the present invention which is concisely described below.

In S1, the log carrying vehicle 4 is pushed to the outside of the shielding door 1 by the locomotive; the locomotive is disconnected; the traction device 6 is hooked automatically with the log carrying vehicle 4; and the shielding door 1 is opened.

In S2, the log carrying vehicle 4 is pulled into the irradiation treatment tunnel 7 by the traction device 6, and the shielding door 1 is closed.

In S3, when the log carrying vehicle 4 nears the accelerators 5, the accelerators 5 generate the beams, the traction device 6 pulls the log carrying vehicle 4 passing through the region of the accelerators 5 reciprocatingly, realizing irradiation treatment of all the logs of the whole vehicle, and after completion of the irradiation treatment of all the logs of the whole vehicle, the X-ray generation stops.

In S4, after completion of the irradiation treatment, the shielding door 1 is opened, and the log carrying vehicle 4 is pulled out of the tunnel 7 by the traction device 6.

In S5, the log carrying vehicle 4 is disconnected from the traction device 6, realizing a cycle of irradiation treatment.

It should be noted that, the particular structure of the device for carrying out the above processes can be varied. For example, in the device with two shielding doors, the log carrying vehicle can enter from the entrance while leaving from the exit. Alternatively, the log carrying vehicle can pass through the irradiation region once, or for several times reciprocatingly.

Although the present embodiment describes a method and a device for conducting irradiation treatment of the logs with X-ray for quarantine purposes, the skilled person can realize that the present invention is applicable to other fields for solving the problems of irradiation and/or quarantine treatment of other goods. Therefore, any modification and application based on the present embodiment perceivable to the skilled person should fall into the protection scope of the present application.

What is claimed is:

1. A method of conducting irradiation with X-rays as a phytosanitary treatment, comprising:
   connecting a traction device and a goods carrying vehicle outside a shielding door;
   opening the shielding door;
   pulling the vehicle into an irradiation treatment tunnel by the traction device;
   closing the shielding door subsequent to entry of the vehicle into the irradiation treatment tunnel;
   upon the vehicle reaching an irradiation region, generating X-rays by accelerators;
   pulling the vehicle by the traction device so that the vehicle passes through the irradiation region to realize irradiation treatment of the whole vehicle;
   subsequent to the irradiation treatment of the whole vehicle, stopping the generation of the X-rays; and
   subsequent to stopping the generation of the X-rays:
      opening the shielding door;
      pulling the vehicle away from the irradiation treatment tunnel by the traction device; and
      disconnecting the traction device from the vehicle;
   wherein the accelerators are a plurality of accelerators arranged symmetrically at opposite sides and at a top of the irradiation region in the tunnel with respect to a cross section that is perpendicular to a direction in which the vehicle is pulled through the tunnel.

2. The method of claim 1, wherein the pulling of the vehicle so that the vehicle passes through the irradiation region includes the traction device pulling the vehicle passing through the radiation region reciprocatingly to receive irradiation twice.

3. The method of claim 1, wherein:
   the plurality of accelerators includes five accelerators;
   two of the five of accelerators are arranged at a left side of the tunnel; and
   two of the five of accelerators are arranged at a right side of the tunnel; and
   one of the five of accelerators is arranged at a top of the tunnel.

4. The method of claim 1, wherein the plurality of accelerators is staggered along the direction in which the vehicle is pulled through the tunnel.

5. The method of claim 1, wherein the goods include logs and different ones of the plurality of accelerators are configured to generate X-rays by electron beams hitting a metal target at different scanning angles with respect to each other, thereby providing an even distribution of an absorbed dose in the logs.

6. The method of claim 1, wherein the goods include logs and the irradiation treatment is conducted for all the logs carried in the vehicle.

7. The method of claim 1, wherein the goods include logs and wherein the arrangement of the accelerators generates an evenly distributed X-ray radiation field in the logs.

8. The method of claim 7, wherein:
   the plurality of accelerators includes five accelerators;
   two of the five of accelerators are arranged at a left side of the tunnel;
   two of the five of accelerators are arranged at a right side of the tunnel; and
   one of the five of accelerators is arranged at a top of the tunnel.

9. The method of claim 7, wherein the plurality of accelerators is staggered along the direction in which the vehicle is pulled through the tunnel.

10. The method of claim 7, wherein different ones of the plurality of accelerators are configured to generate X-rays by electron beams hitting a metal target at different scanning angles with respect to each other, thereby providing an even distribution of an absorbed dose in the logs.

11. A device for conducting irradiation with X-rays as a phytosanitary treatment, comprising:
   a shielding structure having a tunnel formed therethrough;
   a rail provided along the tunnel;
   accelerators within the tunnel; and
   a traction device configured to pull a vehicle carrying goods along the rail for quarantine treatment;
   wherein the accelerators include a plurality of accelerators symmetrically arranged at opposite sides and at a top of an irradiation region in the tunnel with respect to a cross section that is perpendicular to a direction in which the vehicle is pulled within the tunnel.

12. The device of claim 11, wherein:
   the plurality of accelerators includes five accelerators;
   two of the five accelerators are arranged at a left side of the tunnel;
   two of the five accelerators are arranged at a right side of the tunnel; and
   one of the five accelerators is arranged at a top of the tunnel.

13. The device of claim 11, wherein the vehicle carries logs and the goods for quarantine treatment include all the logs carried by the vehicle.

14. The device of claim 13, wherein the shielding structure includes:
   a shielding door provided at an end of the tunnel;
   shielding walls forming the tunnel;
   a maze structure that provides access to the tunnel;
   a radiation source shielding chamber located in the middle of the tunnel and configured to shield leakage radiation of the X-rays generated by the accelerators; and
   a device chamber door that provides access to the radiation source shielding chamber;

wherein the shielding walls are located at opposite sides of and at a first end of the tunnel, and the shielding door is located at a second end of the tunnel opposite the first end.

15. The device of claim 14, wherein each of the shielding door, device chamber door, and maze structure is provided with a safety interlock device configured to prevent unintentional access thereto.

16. The device of claim 14, wherein the shielding door, shielding walls, maze structure, and radiation source shielding chamber form a closed region, which is designated as a radiation controlled area.

17. The device of claim 14, further comprising:
a plurality of buttresses on the shielding walls along the direction in which the vehicle is pulled within the tunnel, wherein the buttresses are arranged to lower a radiation level outside the shielding door caused by scattering of rays on the shielding walls.

18. The device of claim 11, wherein:
the traction device includes a traction locomotive, a hook, a current collector, and a sliding guide rail;
the sliding guide rail is fixed to ground along the direction in which the vehicle is pulled within the tunnel;
the traction device is configured for automatic connection with the vehicle via the hook; and
the current collector is installed on a side of the traction locomotive for contact with the sliding guide rail for keeping communication and supplying a driving power to the traction locomotive.

19. The device of claim 18, wherein the traction device further includes an anti-collision device fixed to an end of the rail in the tunnel, and the anti-collision device is configured and arranged to prevent collision between the traction locomotive and a closed end of the tunnel.

20. The device of claim 18, wherein the traction locomotive is an unmanned automatic driving locomotive.

21. The device of claim 11, wherein:
the goods include logs; and
the plurality of accelerators are configured to generate X-rays by electron beams hitting a metal target at different scanning angles with respect to each other, thereby providing an even distribution of an absorbed dose in the logs.

22. The device of claim 11, wherein energy of the accelerators in use is selected from a range of 10-16 MeV.

23. A method of conducting irradiation with X-rays as a phytosanitary treatment, comprising:
pulling, by the traction device, a vehicle through an irradiation treatment tunnel formed within a shielding structure;
upon the vehicle reaching an irradiation region within the tunnel, generating X-rays by accelerators; and
pulling, by the traction device, the vehicle through the irradiation region to realize irradiation treatment of the whole vehicle;
wherein the accelerators include a plurality of accelerators symmetrically arranged at opposite sides and at a top of the irradiation region with respect to a cross section that is perpendicular to a direction in which the vehicle is pulled within the tunnel.

* * * * *